US008386002B2

(12) United States Patent
Matlock

(10) Patent No.: US 8,386,002 B2
(45) Date of Patent: Feb. 26, 2013

(54) OPTICALLY ALIGNED PULSE OXIMETRY SENSOR AND TECHNIQUE FOR USING THE SAME

(75) Inventor: George L. Matlock, Pleasanton, CA (US)

(73) Assignee: Covidien LP, Mansfield, MA (US)

( * ) Notice: Subject to any disclaimer, the term of this patent is extended or adjusted under 35 U.S.C. 154(b) by 1085 days.

(21) Appl. No.: 12/351,742

(22) Filed: Jan. 9, 2009

(65) Prior Publication Data

US 2009/0118603 A1 May 7, 2009

Related U.S. Application Data

(63) Continuation of application No. 11/241,031, filed on Sep. 30, 2005, now Pat. No. 7,486,979.

(51) Int. Cl.
*A61B 5/1455* (2006.01)
(52) U.S. Cl. ............................... 600/344; 600/323
(58) Field of Classification Search .................. 600/310, 600/322, 323, 344
See application file for complete search history.

(56) References Cited

U.S. PATENT DOCUMENTS

| 3,403,555 | A | 10/1968 | Versaci et al. |
|---|---|---|---|
| 3,536,545 | A | 10/1970 | Traynor et al. |
| D222,454 | S | 10/1971 | Beeber |
| 3,721,813 | A | 3/1973 | Condon et al. |
| 4,098,772 | A | 7/1978 | Bonk et al. |
| D250,275 | S | 11/1978 | Bond |
| D251,387 | S | 3/1979 | Ramsay et al. |
| D262,488 | S | 12/1981 | Rossman et al. |
| 4,334,544 | A | 6/1982 | Hill et al. |
| 4,350,165 | A | 9/1982 | Striese |
| 4,353,372 | A | 10/1982 | Ayer |
| 4,380,240 | A | 4/1983 | Jobsis et al. |
| 4,406,289 | A | 9/1983 | Wesseling et al. |
| 4,510,551 | A | 4/1985 | Brainard, II |
| 4,586,513 | A | 5/1986 | Hamaguri |
| 4,603,700 | A | 8/1986 | Nichols et al. |
| 4,621,643 | A | 11/1986 | New, Jr. et al. |
| 4,653,498 | A | 3/1987 | New, Jr. et al. |
| 4,677,528 | A | 6/1987 | Miniet |
| 4,685,464 | A | 8/1987 | Goldberger et al. |
| 4,694,833 | A | 9/1987 | Hamaguri |
| 4,697,593 | A | 10/1987 | Evans et al. |
| 4,700,708 | A | 10/1987 | New, Jr. et al. |
| 4,714,080 | A | 12/1987 | Edgar, Jr. et al. |
| 4,714,341 | A | 12/1987 | Hamaguri et al. |
| 4,722,120 | A | 2/1988 | Lu |

(Continued)

FOREIGN PATENT DOCUMENTS

| DE | 3405444 | 8/1985 |
|---|---|---|
| DE | 3516338 | 11/1986 |

(Continued)

OTHER PUBLICATIONS

Azhar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

(Continued)

*Primary Examiner* — Eric Winakur
(74) *Attorney, Agent, or Firm* — Fletcher Yoder

(57) ABSTRACT

A physiological sensor is provided that includes an emitter and detector disposed on a frame such that the emitter and detector define an optical axis. The frame includes one or more pair of flexible elements disposed generally symmetric relative to the optical axis. In one embodiment, the emitter and detector remain aligned when moved relative to one another along the optical axis.

20 Claims, 7 Drawing Sheets

U.S. PATENT DOCUMENTS

| | | | |
|---|---|---|---|
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,080,098 A | 1/1992 | Willett et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp, Jr. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakeley et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |

| | | | | | |
|---|---|---|---|---|---|
| 5,392,777 A | 2/1995 | Swedlow et al. | 5,662,106 A | 9/1997 | Swedlow et al. |
| 5,398,680 A | 3/1995 | Polson et al. | 5,664,270 A | 9/1997 | Bell et al. |
| 5,402,777 A | 4/1995 | Warring et al. | 5,666,952 A | 9/1997 | Fuse et al. |
| 5,402,779 A | 4/1995 | Chen et al. | 5,671,529 A | 9/1997 | Nelson |
| 5,411,023 A | 5/1995 | Morris, Sr. et al. | 5,673,692 A | 10/1997 | Schulze et al. |
| 5,411,024 A | 5/1995 | Thomas et al. | 5,673,693 A | 10/1997 | Solenberger |
| 5,413,099 A | 5/1995 | Schmidt et al. | 5,676,139 A | 10/1997 | Goldberger et al. |
| 5,413,100 A | 5/1995 | Barthelemy et al. | 5,676,141 A | 10/1997 | Hollub |
| 5,413,101 A | 5/1995 | Sugiura | 5,678,544 A | 10/1997 | DeLonzor et al. |
| 5,413,102 A | 5/1995 | Schmidt et al. | 5,680,857 A | 10/1997 | Pelikan et al. |
| 5,417,207 A | 5/1995 | Young et al. | 5,685,299 A | 11/1997 | Diab et al. |
| 5,421,329 A | 6/1995 | Casciani et al. | 5,685,301 A | 11/1997 | Klomhaus |
| 5,425,360 A | 6/1995 | Nelson | 5,687,719 A | 11/1997 | Sato et al. |
| 5,425,362 A | 6/1995 | Siker et al. | 5,687,722 A | 11/1997 | Tien et al. |
| 5,427,093 A | 6/1995 | Ogawa et al. | 5,692,503 A | 12/1997 | Kuenstner |
| 5,429,128 A | 7/1995 | Cadell et al. | 5,692,505 A | 12/1997 | Fouts |
| 5,429,129 A | 7/1995 | Lovejoy et al. | 5,709,205 A | 1/1998 | Bukta |
| 5,431,159 A | 7/1995 | Baker et al. | 5,713,355 A | 2/1998 | Richardson et al. |
| 5,431,170 A | 7/1995 | Mathews | 5,724,967 A | 3/1998 | Venkatachalam |
| 5,437,275 A | 8/1995 | Amundsen et al. | 5,727,547 A | 3/1998 | Levinson et al. |
| 5,438,986 A | 8/1995 | Disch et al. | 5,730,124 A | 3/1998 | Yamauchi |
| 5,448,991 A | 9/1995 | Polson et al. | 5,731,582 A | 3/1998 | West |
| 5,452,717 A | 9/1995 | Branigan et al. | D393,830 S | 4/1998 | Tobler et al. |
| 5,465,714 A | 11/1995 | Scheuing | 5,743,260 A | 4/1998 | Chung et al. |
| 5,469,845 A | 11/1995 | DeLonzor et al. | 5,743,262 A | 4/1998 | Lepper, Jr. et al. |
| 5,482,034 A | 1/1996 | Lewis et al. | 5,743,263 A | 4/1998 | Baker, Jr. |
| 5,482,036 A | 1/1996 | Diab et al. | 5,746,206 A | 5/1998 | Mannheimer |
| 5,485,847 A | 1/1996 | Baker, Jr. | 5,746,697 A | 5/1998 | Swedlow et al. |
| 5,490,505 A | 2/1996 | Diab et al. | 5,752,914 A | 5/1998 | DeLonzor et al. |
| 5,490,523 A | 2/1996 | Isaacson et al. | 5,755,226 A | 5/1998 | Carim et al. |
| 5,491,299 A | 2/1996 | Naylor et al. | 5,758,644 A | 6/1998 | Diab et al. |
| 5,494,032 A | 2/1996 | Robinson et al. | 5,760,910 A | 6/1998 | Lepper, Jr. et al. |
| 5,494,043 A | 2/1996 | O'Sullivan et al. | 5,766,125 A | 6/1998 | Aoyagi et al. |
| 5,497,771 A | 3/1996 | Rosenheimer | 5,766,127 A | 6/1998 | Pologe et al. |
| 5,499,627 A | 3/1996 | Steuer et al. | 5,769,785 A | 6/1998 | Diab et al. |
| 5,503,148 A | 4/1996 | Pologe et al. | 5,772,587 A | 6/1998 | Gratton et al. |
| 5,505,199 A | 4/1996 | Kim | 5,774,213 A | 6/1998 | Trebino et al. |
| 5,507,286 A | 4/1996 | Solenberger | 5,776,058 A | 7/1998 | Levinson et al. |
| 5,511,546 A | 4/1996 | Hon | 5,776,059 A | 7/1998 | Kaestle |
| 5,517,988 A | 5/1996 | Gerhard | 5,779,630 A | 7/1998 | Fein et al. |
| 5,520,177 A | 5/1996 | Ogawa et al. | 5,779,631 A | 7/1998 | Chance |
| 5,521,851 A | 5/1996 | Wei et al. | 5,782,237 A | 7/1998 | Casciani et al. |
| 5,522,388 A | 6/1996 | Ishikawa et al. | 5,782,756 A | 7/1998 | Mannheimer |
| 5,524,617 A | 6/1996 | Mannheimer | 5,782,757 A | 7/1998 | Diab et al. |
| 5,529,064 A | 6/1996 | Rall et al. | 5,782,758 A | 7/1998 | Ausec et al. |
| 5,533,507 A | 7/1996 | Potratz et al. | 5,786,592 A | 7/1998 | Hök |
| 5,551,423 A | 9/1996 | Sugiura | 5,788,634 A | 8/1998 | Suda et al. |
| 5,551,424 A | 9/1996 | Morrison et al. | 5,790,729 A | 8/1998 | Pologe et al. |
| 5,553,614 A | 9/1996 | Chance | 5,792,052 A | 8/1998 | Isaacson et al. |
| 5,553,615 A | 9/1996 | Carim et al. | 5,795,292 A | 8/1998 | Lewis et al. |
| 5,555,882 A | 9/1996 | Richardson et al. | 5,797,841 A | 8/1998 | DeLonzor et al. |
| 5,558,096 A | 9/1996 | Palatnik | 5,800,348 A | 9/1998 | Kaestle |
| 5,560,355 A | 10/1996 | Merchant et al. | 5,800,349 A | 9/1998 | Isaacson et al. |
| 5,564,417 A | 10/1996 | Chance | 5,803,910 A | 9/1998 | Potratz |
| 5,575,284 A | 11/1996 | Athan et al. | 5,807,246 A | 9/1998 | Sakaguchi et al. |
| 5,575,285 A | 11/1996 | Takanashi et al. | 5,807,247 A | 9/1998 | Merchant et al. |
| 5,577,500 A | 11/1996 | Potratz | 5,807,248 A | 9/1998 | Mills |
| 5,582,169 A | 12/1996 | Oda et al. | 5,810,723 A | 9/1998 | Aldrich |
| 5,584,296 A | 12/1996 | Cui et al. | 5,810,724 A | 9/1998 | Gronvall |
| 5,588,425 A | 12/1996 | Sackner et al. | 5,813,980 A | 9/1998 | Levinson et al. |
| 5,588,427 A | 12/1996 | Tien | 5,817,008 A | 10/1998 | Rafert et al. |
| 5,590,652 A | 1/1997 | Inai | 5,817,009 A | 10/1998 | Rosenheimer et al. |
| 5,595,176 A | 1/1997 | Yamaura | 5,817,010 A | 10/1998 | Hibl |
| 5,596,986 A | 1/1997 | Goldfarb | 5,818,985 A | 10/1998 | Merchant et al. |
| 5,611,337 A | 3/1997 | Bukta | 5,820,550 A | 10/1998 | Polson et al. |
| 5,617,852 A | 4/1997 | MacGregor | 5,823,950 A | 10/1998 | Diab et al. |
| 5,619,992 A | 4/1997 | Guthrie et al. | 5,823,952 A | 10/1998 | Levinson et al. |
| 5,626,140 A | 5/1997 | Feldman et al. | 5,827,179 A | 10/1998 | Lichter et al. |
| 5,630,413 A | 5/1997 | Thomas et al. | 5,827,182 A | 10/1998 | Raley et al. |
| 5,632,272 A | 5/1997 | Diab et al. | 5,829,439 A | 11/1998 | Yokosawa et al. |
| 5,632,273 A | 5/1997 | Suzuki | 5,830,135 A | 11/1998 | Bosque et al. |
| 5,634,459 A | 6/1997 | Gardosi | 5,830,136 A | 11/1998 | DeLonzor et al. |
| 5,638,593 A | 6/1997 | Gerhardt et al. | 5,830,137 A | 11/1998 | Scharf |
| 5,638,816 A | 6/1997 | Kiani-Azarbayjany et al. | 5,839,439 A | 11/1998 | Nierlich et al. |
| 5,638,818 A | 6/1997 | Diab et al. | 5,842,979 A | 12/1998 | Jarman et al. |
| 5,645,060 A | 7/1997 | Yorkey et al. | 5,842,981 A | 12/1998 | Larsen et al. |
| 5,645,440 A | 7/1997 | Tobler et al. | 5,842,982 A | 12/1998 | Mannheimer |
| 5,660,567 A | 8/1997 | Nierlich et al. | 5,846,190 A | 12/1998 | Woehrle |
| 5,662,105 A | 9/1997 | Tien | 5,851,178 A | 12/1998 | Aronow |

| Patent No. | Date | Inventor |
|---|---|---|
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Weil et al. |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,829 A | 6/2000 | Uchida |
| 6,078,833 A | 6/2000 | Hueber |
| 6,081,735 A | 6/2000 | Diab et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner et al. |
| 6,112,107 A | 8/2000 | Hannula |
| 6,113,541 A | 9/2000 | Dias et al. |
| 6,115,621 A | 9/2000 | Chin |
| 6,122,535 A | 9/2000 | Kaestle et al. |
| 6,133,994 A | 10/2000 | Mathews et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllerman et al. |
| 6,151,516 A | 11/2000 | Kiani-Azarbayjani et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter et al. |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |

| | | | | | | |
|---|---|---|---|---|---|---|
| 6,370,408 B1 | 4/2002 | Merchant et al. | | 6,591,122 B2 | 7/2003 | Schmitt |
| 6,370,409 B1 | 4/2002 | Chung et al. | | 6,591,123 B2 | 7/2003 | Fein et al. |
| 6,371,921 B1 | 4/2002 | Caro | | 6,594,511 B2 | 7/2003 | Stone et al. |
| 6,374,129 B1 | 4/2002 | Chin et al. | | 6,594,512 B2 | 7/2003 | Huang |
| 6,377,829 B1 | 4/2002 | Al-Ali et al. | | 6,594,513 B1 | 7/2003 | Jobsis et al. |
| 6,381,479 B1 | 4/2002 | Norris | | 6,597,931 B1 | 7/2003 | Cheng et al. |
| 6,381,480 B1 | 4/2002 | Stoddart et al. | | 6,597,933 B2 | 7/2003 | Kiani et al. |
| 6,385,471 B1 | 5/2002 | Mortz | | 6,600,940 B1 | 7/2003 | Fein et al. |
| 6,385,821 B1 | 5/2002 | Modgil et al. | | 6,606,510 B2 | 8/2003 | Swedlow et al. |
| 6,388,240 B2 | 5/2002 | Schulz et al. | | 6,606,511 B1 | 8/2003 | Ali et al. |
| 6,393,310 B1 | 5/2002 | Kuenster | | 6,606,512 B2 | 8/2003 | Muz et al. |
| 6,393,311 B1 | 5/2002 | Edgar, Jr. et al. | | 6,608,562 B1 | 8/2003 | Kimura et al. |
| 6,397,091 B2 | 5/2002 | Diab et al. | | 6,609,016 B1 | 8/2003 | Lynn |
| 6,397,092 B1 | 5/2002 | Norris et al. | | 6,615,064 B1 | 9/2003 | Aldrich |
| 6,397,093 B1 | 5/2002 | Aldrich | | 6,615,065 B1 | 9/2003 | Barrett et al. |
| 6,400,971 B1 | 6/2002 | Finarov et al. | | 6,618,602 B2 | 9/2003 | Levin et al. |
| 6,400,972 B1 | 6/2002 | Fine | | 6,622,034 B1 | 9/2003 | Gorski et al. |
| 6,400,973 B1 | 6/2002 | Winter | | 6,628,975 B1 | 9/2003 | Fein et al. |
| 6,402,690 B1 | 6/2002 | Rhee et al. | | 6,631,281 B1 | 10/2003 | Kästle |
| 6,408,198 B1 | 6/2002 | Hanna et al. | | 6,632,181 B2 | 10/2003 | Flaherty |
| 6,411,832 B1 | 6/2002 | Guthermann | | 6,640,116 B2 | 10/2003 | Diab |
| 6,411,833 B1 | 6/2002 | Baker, Jr. et al. | | 6,643,530 B2 | 11/2003 | Diab et al. |
| 6,421,549 B1 | 7/2002 | Jacques | | 6,643,531 B1 | 11/2003 | Katarow |
| 6,430,423 B2 | 8/2002 | DeLonzor et al. | | 6,647,279 B2 | 11/2003 | Pologe |
| 6,430,513 B1 | 8/2002 | Wang et al. | | 6,647,280 B2 | 11/2003 | Bahr et al. |
| 6,430,525 B1 | 8/2002 | Weber et al. | | 6,650,916 B2 | 11/2003 | Cook |
| 6,434,408 B1 | 8/2002 | Heckel et al. | | 6,650,917 B2 | 11/2003 | Diab et al. |
| 6,438,396 B1 | 8/2002 | Cook | | 6,650,918 B2 | 11/2003 | Terry |
| 6,438,399 B1 | 8/2002 | Kurth | | 6,654,621 B2 | 11/2003 | Palatnik et al. |
| 6,449,501 B1 | 9/2002 | Reuss | | 6,654,622 B1 | 11/2003 | Eberhard et al. |
| 6,453,183 B1 | 9/2002 | Walker | | 6,654,623 B1 | 11/2003 | Kästle |
| 6,453,184 B1 | 9/2002 | Hyogo et al. | | 6,654,624 B2 | 11/2003 | Diab et al. |
| 6,456,862 B2 | 9/2002 | Benni | | 6,658,276 B2 | 12/2003 | Kianl et al. |
| 6,461,305 B1 | 10/2002 | Schnall | | 6,658,277 B2 | 12/2003 | Wassermann |
| 6,463,310 B1 | 10/2002 | Swedlow et al. | | 6,662,033 B2 | 12/2003 | Casciani et al. |
| 6,463,311 B1 | 10/2002 | Diab | | 6,665,551 B1 | 12/2003 | Suzuki |
| 6,466,808 B1 | 10/2002 | Chin et al. | | 6,668,182 B2 | 12/2003 | Hubelbank |
| 6,466,809 B1 | 10/2002 | Riley | | 6,668,183 B2 | 12/2003 | Hicks et al. |
| 6,470,199 B1 | 10/2002 | Kopotic et al. | | 6,671,526 B1 | 12/2003 | Aoyagi et al. |
| 6,470,200 B2 | 10/2002 | Walker et al. | | 6,671,528 B2 | 12/2003 | Steuer et al. |
| 6,480,729 B2 | 11/2002 | Stone | | 6,671,530 B2 | 12/2003 | Chung et al. |
| 6,490,466 B1 | 12/2002 | Fein et al. | | 6,671,531 B2 | 12/2003 | Al-Ali et al. |
| 6,493,568 B1 | 12/2002 | Bell | | 6,671,532 B1 | 12/2003 | Fudge et al. |
| 6,496,711 B1 | 12/2002 | Athan et al. | | 6,675,031 B1 | 1/2004 | Porges et al. |
| 6,498,942 B1 | 12/2002 | Esenaliev et al. | | 6,678,543 B2 | 1/2004 | Diab et al. |
| 6,501,974 B2 | 12/2002 | Huiku | | 6,681,126 B2 | 1/2004 | Solenberger |
| 6,501,975 B2 | 12/2002 | Diab et al. | | 6,681,128 B2 | 1/2004 | Steuer et al. |
| 6,505,060 B1 | 1/2003 | Norris | | 6,681,454 B2 | 1/2004 | Modgil et al. |
| 6,505,061 B2 | 1/2003 | Larson | | 6,684,090 B2 | 1/2004 | Ali et al. |
| 6,505,133 B1 | 1/2003 | Hanna et al. | | 6,684,091 B2 | 1/2004 | Parker |
| 6,510,329 B2 | 1/2003 | Heckel | | 6,694,160 B2 | 2/2004 | Chin |
| 6,510,331 B1 | 1/2003 | Williams et al. | | 6,697,653 B2 | 2/2004 | Hanna |
| 6,512,937 B2 | 1/2003 | Blank et al. | | 6,697,655 B2 | 2/2004 | Sueppel et al. |
| 6,515,273 B2 | 2/2003 | Al-Ali | | 6,697,656 B1 | 2/2004 | Al-Ali |
| 6,519,484 B1 | 2/2003 | Lovejoy et al. | | 6,697,658 B2 | 2/2004 | Al-Ali |
| 6,519,486 B1 | 2/2003 | Edgar, Jr. et al. | | RE38,476 E | 3/2004 | Diab et al. |
| 6,519,487 B1 | 2/2003 | Parker | | 6,699,194 B1 | 3/2004 | Diab et al. |
| 6,525,386 B1 | 2/2003 | Mills et al. | | 6,699,199 B2 | 3/2004 | Asada et al. |
| 6,526,300 B1 | 2/2003 | Kiani et al. | | 6,701,170 B2 | 3/2004 | Stetson |
| 6,526,301 B2 | 2/2003 | Larsen et al. | | 6,702,752 B2 | 3/2004 | Dekker |
| 6,541,756 B2 | 4/2003 | Schulz et al. | | 6,707,257 B2 | 3/2004 | Norris |
| 6,542,764 B1 | 4/2003 | Al-Ali et al. | | 6,708,049 B1 | 3/2004 | Berson et al. |
| 6,546,267 B1 | 4/2003 | Sugiura et al. | | 6,709,402 B2 | 3/2004 | Dekker |
| 6,553,241 B2 | 4/2003 | Mannheimer et al. | | 6,711,424 B1 | 3/2004 | Fine et al. |
| 6,553,242 B1 | 4/2003 | Sarussi | | 6,711,425 B1 | 3/2004 | Reuss |
| 6,553,243 B2 | 4/2003 | Gurley | | 6,712,762 B1 | 3/2004 | Lichter et al. |
| 6,554,788 B1 | 4/2003 | Hunley | | 6,714,803 B1 | 3/2004 | Mortz |
| 6,556,852 B1 | 4/2003 | Schulze et al. | | 6,714,804 B2 | 3/2004 | Al-Ali et al. |
| 6,560,470 B1 | 5/2003 | Pologe | | 6,714,805 B2 | 3/2004 | Jeon et al. |
| 6,564,077 B2 | 5/2003 | Mortara | | RE38,492 E | 4/2004 | Diab et al. |
| 6,564,088 B1 | 5/2003 | Soller et al. | | 6,719,686 B2 | 4/2004 | Coakley et al. |
| 6,571,113 B1 | 5/2003 | Fein et al. | | 6,719,705 B2 | 4/2004 | Mills |
| 6,571,114 B1 | 5/2003 | Koike et al. | | 6,720,734 B2 | 4/2004 | Norris |
| 6,574,491 B2 | 6/2003 | Elghazzawi | | 6,721,584 B2 | 4/2004 | Baker, Jr. et al. |
| 6,580,086 B1 | 6/2003 | Schulz et al. | | 6,721,585 B1 | 4/2004 | Parker |
| 6,584,336 B1 | 6/2003 | Ali et al. | | 6,725,074 B1 | 4/2004 | Kästle |
| 6,587,703 B2 | 7/2003 | Cheng et al. | | 6,725,075 B2 | 4/2004 | Al-Ali |
| 6,587,704 B1 | 7/2003 | Fine et al. | | 6,731,962 B1 | 5/2004 | Katarow |
| 6,589,172 B2 | 7/2003 | Williams et al. | | 6,731,963 B2 | 5/2004 | Finarov et al. |

| Patent | Date | Name |
|---|---|---|
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,963,767 B2 | 11/2005 | Rantala et al. |
| 6,968,221 B2 | 11/2005 | Rosenthal |
| 6,979,812 B2 | 12/2005 | Al-Ali |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,039,449 B2 | 5/2006 | Al-Ali |
| 7,043,289 B2 | 5/2006 | Fine et al. |
| 7,047,055 B2 | 5/2006 | Boas et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,190,987 B2 | 3/2007 | Lindekugel et al. |
| 7,198,778 B2 | 4/2007 | Achilefu et al. |
| 7,215,984 B2 | 5/2007 | Diab et al. |
| 7,225,006 B2 | 5/2007 | Al-Ali et al. |
| 7,228,161 B2 | 6/2007 | Chin |
| 7,236,811 B2 | 6/2007 | Schmitt |
| 7,248,910 B2 | 7/2007 | Li et al. |
| 7,254,433 B2 | 8/2007 | Diab et al. |
| 7,254,434 B2 | 8/2007 | Schulz et al. |
| 7,263,395 B2 | 8/2007 | Chan et al. |
| 7,272,426 B2 | 9/2007 | Schmid |
| 7,280,858 B2 | 10/2007 | Al-Ali et al. |
| 7,295,866 B2 | 11/2007 | Al-Ali et al. |
| 7,305,262 B2 | 12/2007 | Brodnick et al. |
| 7,315,753 B2 | 1/2008 | Baker, Jr. et al. |
| 7,486,979 B2 | 2/2009 | Matlock |
| 7,590,439 B2 | 9/2009 | Raridan et al. |
| 2001/0021803 A1 | 9/2001 | Blank et al. |
| 2001/0051767 A1 | 12/2001 | Williams et al. |
| 2002/0016537 A1 | 2/2002 | Muz et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnall |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0018243 A1 | 1/2003 | Gerhardt et al. |
| 2003/0036690 A1 | 2/2003 | Geddes et al. |
| 2003/0045784 A1 | 3/2003 | Palatnik et al. |
| 2003/0045785 A1 | 3/2003 | Diab et al. |
| 2003/0073889 A1 | 4/2003 | Keilbach et al. |
| 2003/0073890 A1 | 4/2003 | Hanna |
| 2003/0100840 A1 | 5/2003 | Sugiura et al. |
| 2003/0132495 A1 | 7/2003 | Mills et al. |
| 2003/0135099 A1 | 7/2003 | Al-Ali |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0181799 A1 | 9/2003 | Lindekugel et al. |
| 2003/0187337 A1 | 10/2003 | Tarassenko et al. |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2003/0225337 A1 | 12/2003 | Scharf et al. |

| | | |
|---|---|---|
| 2003/0236452 A1 | 12/2003 | Melker et al. |
| 2003/0236647 A1 | 12/2003 | Yoon et al. |
| 2004/0006261 A1 | 1/2004 | Swedlow et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0054269 A1 | 3/2004 | Rantala et al. |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |
| 2004/0068164 A1 | 4/2004 | Diab et al. |
| 2004/0087846 A1 | 5/2004 | Wasserman |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0107065 A1 | 6/2004 | Al-Ali et al. |
| 2004/0116788 A1 | 6/2004 | Chernoguz et al. |
| 2004/0116789 A1 | 6/2004 | Boas et al. |
| 2004/0117891 A1 | 6/2004 | Hannula et al. |
| 2004/0122300 A1 | 6/2004 | Boas et al. |
| 2004/0122302 A1 | 6/2004 | Mason et al. |
| 2004/0133087 A1 | 7/2004 | Ali et al. |
| 2004/0133088 A1 | 7/2004 | Al-Ali et al. |
| 2004/0138538 A1 | 7/2004 | Stetson |
| 2004/0138540 A1 | 7/2004 | Baker, Jr. et al. |
| 2004/0143172 A1 | 7/2004 | Fudge et al. |
| 2004/0147821 A1 | 7/2004 | Al-Ali et al. |
| 2004/0147822 A1 | 7/2004 | Al-Ali et al. |
| 2004/0147823 A1 | 7/2004 | Kiani et al. |
| 2004/0147824 A1 | 7/2004 | Diab et al. |
| 2004/0152965 A1 | 8/2004 | Diab et al. |
| 2004/0158134 A1 | 8/2004 | Diab et al. |
| 2004/0158135 A1 | 8/2004 | Baker, Jr. et al. |
| 2004/0162472 A1 | 8/2004 | Berson et al. |
| 2004/0167381 A1 | 8/2004 | Lichter |
| 2004/0171920 A1 | 9/2004 | Mannheimer et al. |
| 2004/0171948 A1 | 9/2004 | Terry |
| 2004/0176671 A1 | 9/2004 | Fine et al. |
| 2004/0181133 A1 | 9/2004 | Al-Ali et al. |
| 2004/0181134 A1 | 9/2004 | Baker, Jr. et al. |
| 2004/0186358 A1 | 9/2004 | Chernow et al. |
| 2004/0199063 A1 | 10/2004 | O'Neil et al. |
| 2004/0204636 A1 | 10/2004 | Diab et al. |
| 2004/0204637 A1 | 10/2004 | Diab et al. |
| 2004/0204865 A1 | 10/2004 | Lee et al. |
| 2004/0210146 A1 | 10/2004 | Diab et al. |
| 2004/0215069 A1 | 10/2004 | Mannheimer |
| 2004/0215085 A1 | 10/2004 | Schnall |
| 2004/0230107 A1 | 11/2004 | Asada et al. |
| 2004/0230108 A1 | 11/2004 | Melker et al. |
| 2004/0236196 A1 | 11/2004 | Diab et al. |
| 2004/0242980 A1 | 12/2004 | Kiani et al. |
| 2004/0249252 A1 | 12/2004 | Fine et al. |
| 2004/0257557 A1 | 12/2004 | Block et al. |
| 2004/0260161 A1 | 12/2004 | Melker et al. |
| 2004/0267103 A1 | 12/2004 | Li et al. |
| 2004/0267104 A1 | 12/2004 | Hannula et al. |
| 2004/0267140 A1 | 12/2004 | Ito et al. |
| 2005/0004479 A1 | 1/2005 | Townsend et al. |
| 2005/0010092 A1 | 1/2005 | Weber et al. |
| 2005/0014999 A1 | 1/2005 | Rahe-Meyer |
| 2005/0020887 A1 | 1/2005 | Goldberg |
| 2005/0020894 A1 | 1/2005 | Norris et al. |
| 2005/0033131 A1 | 2/2005 | Chen et al. |
| 2005/0043599 A1 | 2/2005 | O'Mara |
| 2005/0043600 A1 | 2/2005 | Diab et al. |
| 2005/0049468 A1 | 3/2005 | Carlson |
| 2005/0049470 A1 | 3/2005 | Terry |
| 2005/0049471 A1 | 3/2005 | Aceti |
| 2005/0070773 A1 | 3/2005 | Chin |
| 2005/0075546 A1 | 4/2005 | Samsoondar |
| 2005/0075550 A1 | 4/2005 | Lindekugel |
| 2005/0085704 A1 | 4/2005 | Schulz |
| 2005/0090720 A1 | 4/2005 | Wu |
| 2005/0197548 A1 | 9/2005 | Dietiker |
| 2005/0228248 A1 | 10/2005 | Dietiker |
| 2005/0256386 A1 | 11/2005 | Chan |
| 2005/0277819 A1 | 12/2005 | Kiani et al. |
| 2006/0020179 A1 | 1/2006 | Anderson |
| 2006/0030764 A1 | 2/2006 | Porges |
| 2006/0058594 A1 | 3/2006 | Ishizuka et al. |
| 2006/0074280 A1 | 4/2006 | Martis |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122517 A1 | 6/2006 | Banet |
| 2006/0129039 A1 | 6/2006 | Lindner |
| 2006/0155198 A1 | 7/2006 | Schmid |
| 2006/0173257 A1 | 8/2006 | Nagai |
| 2007/0032707 A1 | 2/2007 | Coakley et al. |
| 2007/0032708 A1 | 2/2007 | Eghbal et al. |
| 2007/0032711 A1 | 2/2007 | Coakley et al. |
| 2007/0032712 A1 | 2/2007 | Raridan et al. |
| 2007/0032713 A1 | 2/2007 | Eghbal et al. |
| 2007/0032715 A1 | 2/2007 | Eghbal et al. |
| 2007/0032716 A1 | 2/2007 | Raridan et al. |
| 2007/0073126 A1 | 3/2007 | Raridan, Jr. |

FOREIGN PATENT DOCUMENTS

| | | |
|---|---|---|
| DE | 3703458 | 8/1988 |
| DE | 4210102 | 9/1993 |
| DE | 19632361 | 2/1997 |
| DE | 69123448 | 5/1997 |
| DE | 19703220 | 7/1997 |
| DE | 19640807 | 9/1997 |
| DE | 19647877 | 4/1998 |
| DE | 10030862 | 1/2002 |
| DE | 20318882 | 4/2004 |
| EP | 0127947 | 5/1984 |
| EP | 194105 | 9/1986 |
| EP | 0204459 | 12/1986 |
| EP | 0315040 | 10/1988 |
| EP | 0314331 | 5/1989 |
| EP | 0352923 | 1/1990 |
| EP | 0430340 | 6/1991 |
| EP | 0572684 | 5/1992 |
| EP | 00497021 | 8/1992 |
| EP | 0529412 | 8/1992 |
| EP | 0531631 | 9/1992 |
| EP | 0566354 | 4/1993 |
| EP | 0587009 | 8/1993 |
| EP | 0615723 | 9/1994 |
| EP | 0702931 | 3/1996 |
| EP | 0724860 | 8/1996 |
| EP | 0793942 | 9/1997 |
| EP | 0875199 | 11/1998 |
| EP | 1332713 | 8/2003 |
| EP | 1491135 | 12/2004 |
| FR | 2685865 | 1/1992 |
| JP | 63275325 | 11/1988 |
| JP | 2013450 | 1/1990 |
| JP | 2111343 | 4/1990 |
| JP | 2237544 | 9/1990 |
| JP | 3170866 | 7/1991 |
| JP | 3173536 | 7/1991 |
| JP | 3245042 | 10/1991 |
| JP | 4174648 | 6/1992 |
| JP | 4191642 | 7/1992 |
| JP | 4332536 | 11/1992 |
| JP | 3124073 | 3/1993 |
| JP | 5049624 | 3/1993 |
| JP | 5049625 | 3/1993 |
| JP | 3115374 | 4/1993 |
| JP | 5212016 | 8/1993 |
| JP | 6014906 | 1/1994 |
| JP | 6016774 | 3/1994 |
| JP | 3116255 | 4/1994 |
| JP | 6029504 | 4/1994 |
| JP | 6098881 | 4/1994 |
| JP | 6154177 | 6/1994 |
| JP | 6269430 | 9/1994 |
| JP | 6285048 | 10/1994 |
| JP | 7001273 | 1/1995 |

| | | |
|---|---:|---|
| JP | 7124138 | 5/1995 |
| JP | 7136150 | 5/1995 |
| JP | 7155311 | 6/1995 |
| JP | 7155313 | 6/1995 |
| JP | 7171139 | 7/1995 |
| JP | 7236625 | 9/1995 |
| JP | 7246191 | 9/1995 |
| JP | 8256996 | 10/1996 |
| JP | 9192120 | 7/1997 |
| JP | 10216113 | 8/1998 |
| JP | 10216114 | 8/1998 |
| JP | 10216115 | 8/1998 |
| JP | 10337282 | 12/1998 |
| JP | 11019074 | 1/1999 |
| JP | 11155841 | 6/1999 |
| JP | 11244268 | 9/1999 |
| JP | 2000107157 | 4/2000 |
| JP | 2000237170 | 9/2000 |
| JP | 3116259 | 10/2000 |
| JP | 3116260 | 10/2000 |
| JP | 3134144 | 12/2000 |
| JP | 2001245871 | 9/2001 |
| JP | 3238813 | 10/2001 |
| JP | 2002224088 | 8/2002 |
| JP | 2002282242 | 10/2002 |
| JP | 2003153881 | 5/2003 |
| JP | 2003153882 | 5/2003 |
| JP | 2003169791 | 6/2003 |
| JP | 2003194714 | 7/2003 |
| JP | 2003210438 | 7/2003 |
| JP | 2003275192 | 9/2003 |
| JP | 2003339678 | 12/2003 |
| JP | 2004008572 | 1/2004 |
| JP | 2004089546 | 3/2004 |
| JP | 2004113353 | 4/2004 |
| JP | 2004135854 | 5/2004 |
| JP | 2004148069 | 5/2004 |
| JP | 2004148070 | 5/2004 |
| JP | 2004159810 | 6/2004 |
| JP | 2004166775 | 6/2004 |
| JP | 2004194908 | 7/2004 |
| JP | 2004202190 | 7/2004 |
| JP | 2004248819 | 9/2004 |
| JP | 2004248820 | 9/2004 |
| JP | 2004261364 | 9/2004 |
| JP | 2004290412 | 10/2004 |
| JP | 2004290544 | 10/2004 |
| JP | 2004290545 | 10/2004 |
| JP | 2004329406 | 11/2004 |
| JP | 2004329607 | 11/2004 |
| JP | 2004329928 | 11/2004 |
| JP | 2004337605 | 12/2004 |
| JP | 2004344367 | 12/2004 |
| JP | 2004351107 | 12/2004 |
| JP | 2005034472 | 2/2005 |
| JP | 2005200031 | 7/2005 |
| WO | WO98/09566 | 10/1989 |
| WO | WO9001293 | 2/1990 |
| WO | WO9004352 | 5/1990 |
| WO | WO9101678 | 2/1991 |
| WO | WO9111137 | 8/1991 |
| WO | WO9200513 | 1/1992 |
| WO | WO9221281 | 12/1992 |
| WO | WO9309711 | 5/1993 |
| WO | WO9313706 | 7/1993 |
| WO | WO9316629 | 9/1993 |
| WO | WO9403102 | 2/1994 |
| WO | WO9423643 | 10/1994 |
| WO | WO9502358 | 1/1995 |
| WO | WO9512349 | 5/1995 |
| WO | WO9613208 | 5/1996 |
| WO | WO9639927 | 12/1996 |
| WO | WO9736536 | 10/1997 |
| WO | WO9749330 | 12/1997 |
| WO | WO9817174 | 4/1998 |
| WO | WO9818382 | 5/1998 |
| WO | WO9842249 | 10/1998 |
| WO | WO9842251 | 10/1998 |
| WO | WO9843071 | 10/1998 |
| WO | WO9851212 | 11/1998 |
| WO | WO9857577 | 12/1998 |
| WO | WO9932030 | 7/1999 |
| WO | WO9947039 | 9/1999 |
| WO | WO0021438 | 4/2000 |
| WO | WO0028888 | 5/2000 |
| WO | WO0059374 | 10/2000 |
| WO | WO0113790 | 3/2001 |
| WO | WO0116577 | 3/2001 |
| WO | WO0117421 | 3/2001 |
| WO | WO0140776 | 6/2001 |
| WO | WO0147426 | 7/2001 |
| WO | WO0176461 | 10/2001 |
| WO | WO0214793 | 2/2002 |
| WO | WO0235999 | 5/2002 |
| WO | WO02062213 | 8/2002 |
| WO | WO02074162 | 9/2002 |
| WO | WO03000125 | 1/2003 |
| WO | WO03001180 | 1/2003 |
| WO | WO03009750 | 2/2003 |
| WO | WO03011127 | 2/2003 |
| WO | WO03039326 | 5/2003 |
| WO | WO03073924 | 9/2003 |
| WO | WO2004000114 | 12/2003 |
| WO | WO2004006748 | 1/2004 |
| WO | WO2004075746 | 9/2004 |
| WO | WO2005002434 | 1/2005 |
| WO | WO2005009221 | 2/2005 |
| WO | WO2005010567 | 2/2005 |
| WO | WO2005010568 | 2/2005 |
| WO | WO2005020120 | 3/2005 |
| WO | WO2005065540 | 7/2005 |
| WO | WO2006104790 | 10/2006 |

OTHER PUBLICATIONS

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30—Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

Dekock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1999).

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Lopez-Silva, Sonnia Maria, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earterowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shalt'S, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, SpO2, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Lopez-Silva, Sonnia Maria, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the $25^{th}$ Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Mendelson, Y., et al.; "Measurement Site and Photodetector Size Considerations in Optimizing Power Consumption of a Wearable Reflectance Pulse Oximeter," *Proceedings of the $25^{th}$ Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the $25^{th}$ Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the $25^{th}$ Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

Johansson; A.; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger SpO_2 recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

Hayoz, J., et al.; "World's First Combined digital Pulse Oximetry Pulse Oximetry and Carbon Dioxide Tension Ear Sensor", *Abstracts*, A6, p. S103. (undated).

Huang, J.,et al.; "Low Power Motion Tolerant Pulse Oximetry," *Abstracts*, A7, p. S103. (undated).

Lang, P., et al.; "Signal Identification and Quality Indicator™ for Motion Resistant Pulse Oximetry," *Abstracts*, A10, p. S105. (undated).

Neumann, R. et al.; "Fourier Artifact suppression Technology Provides Reliable $SpO_2$," *Abstracts*, A11, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

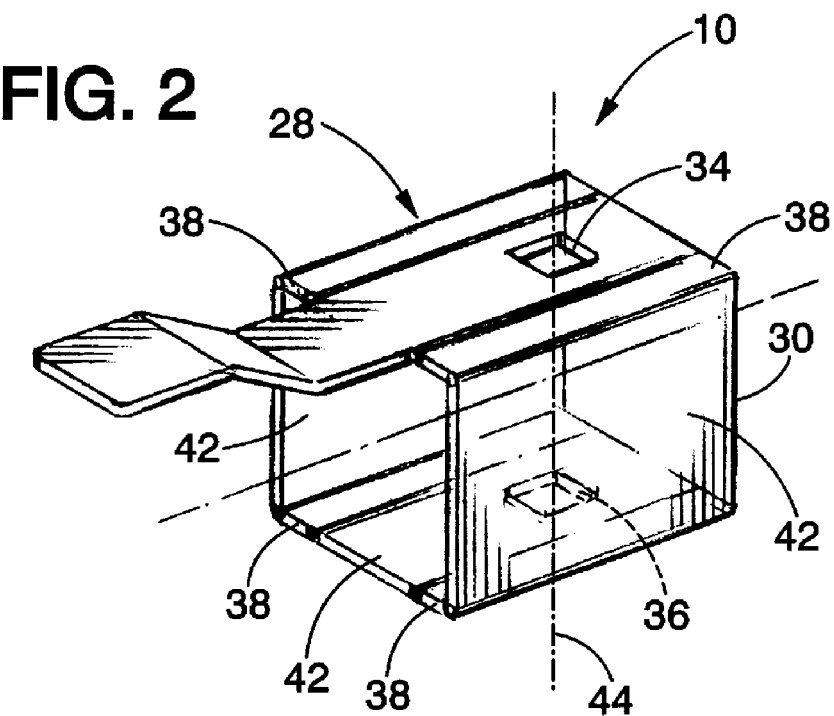
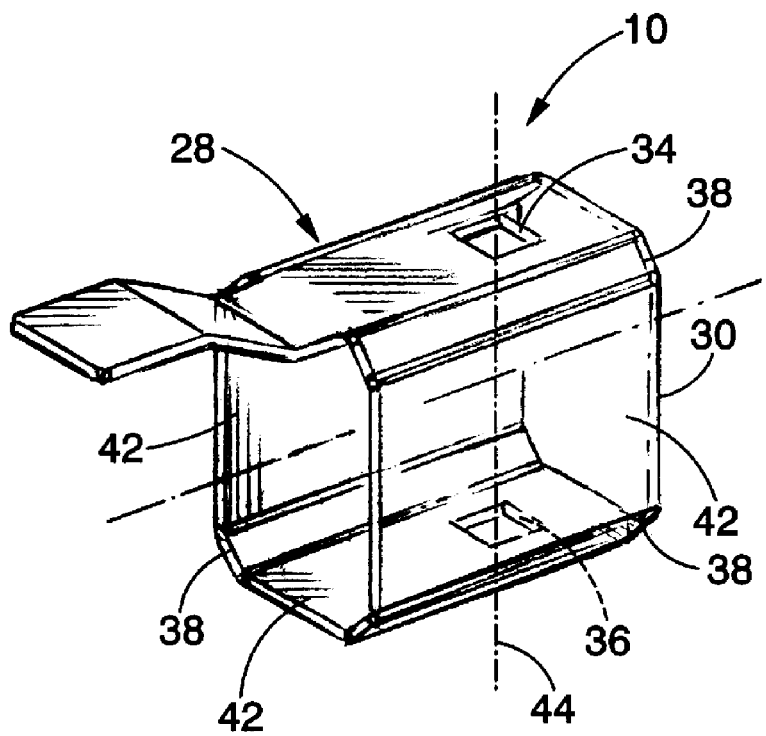

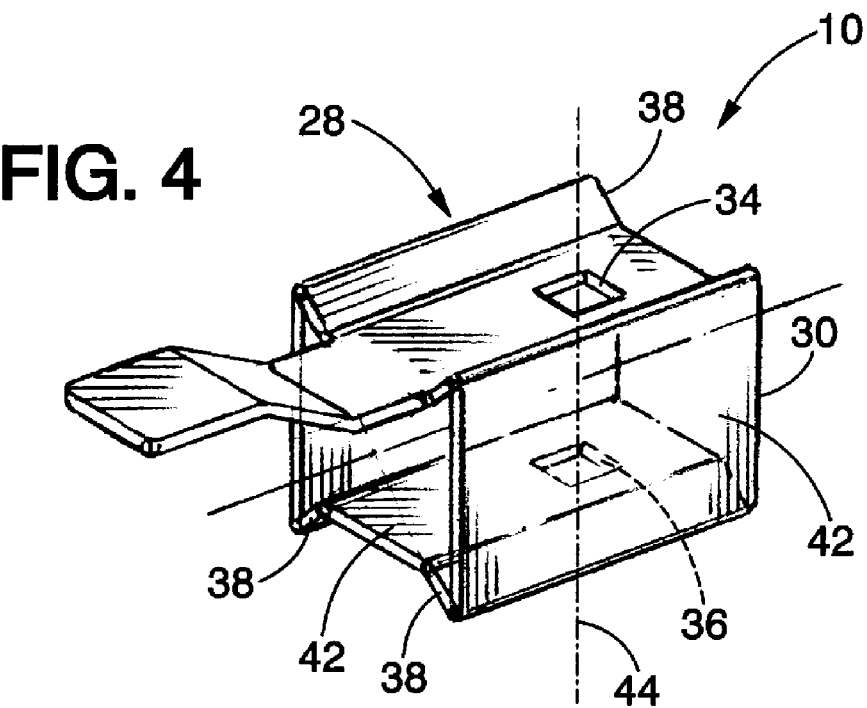
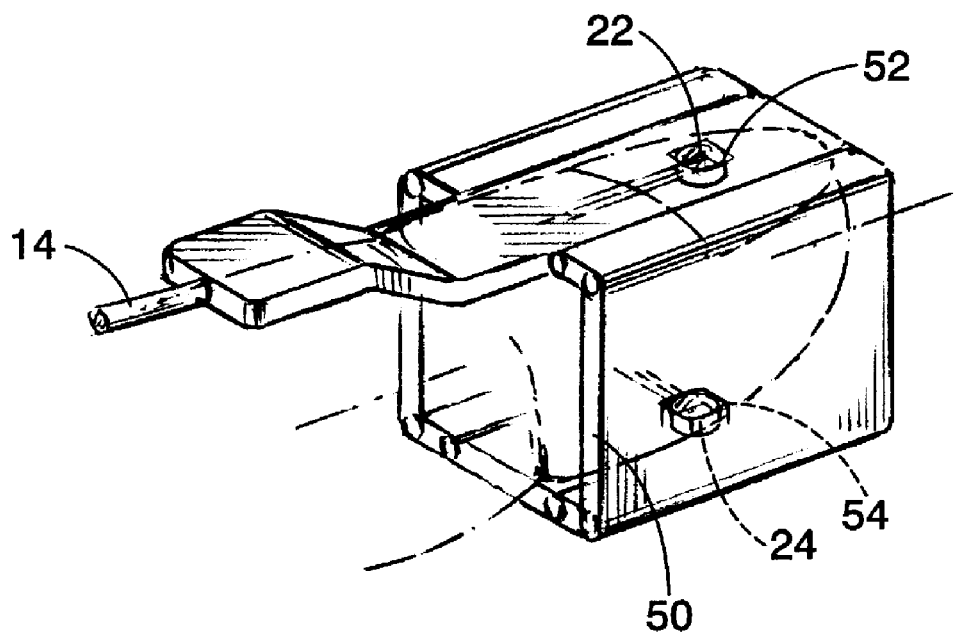

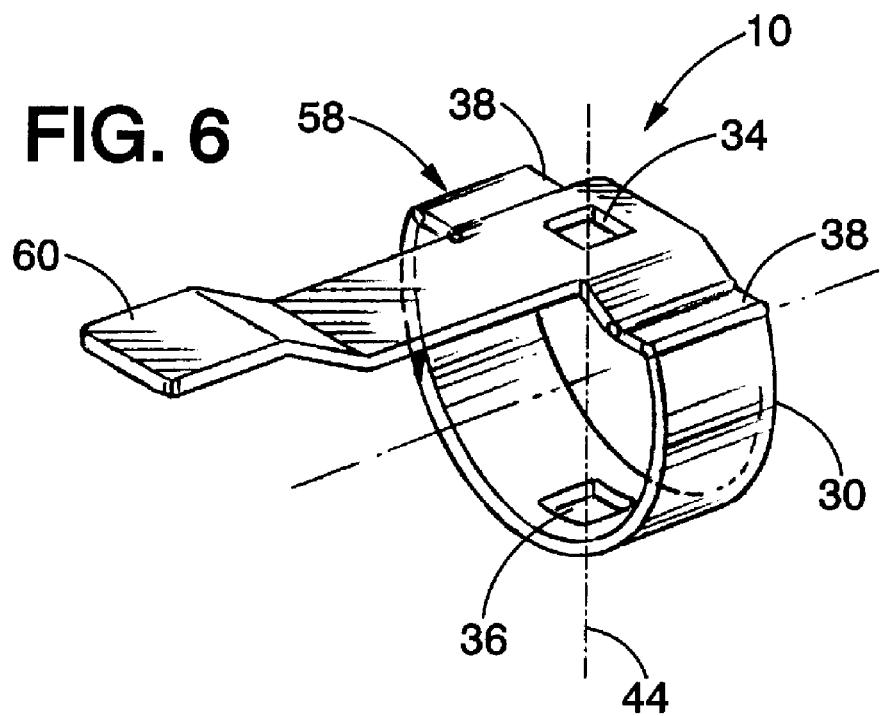
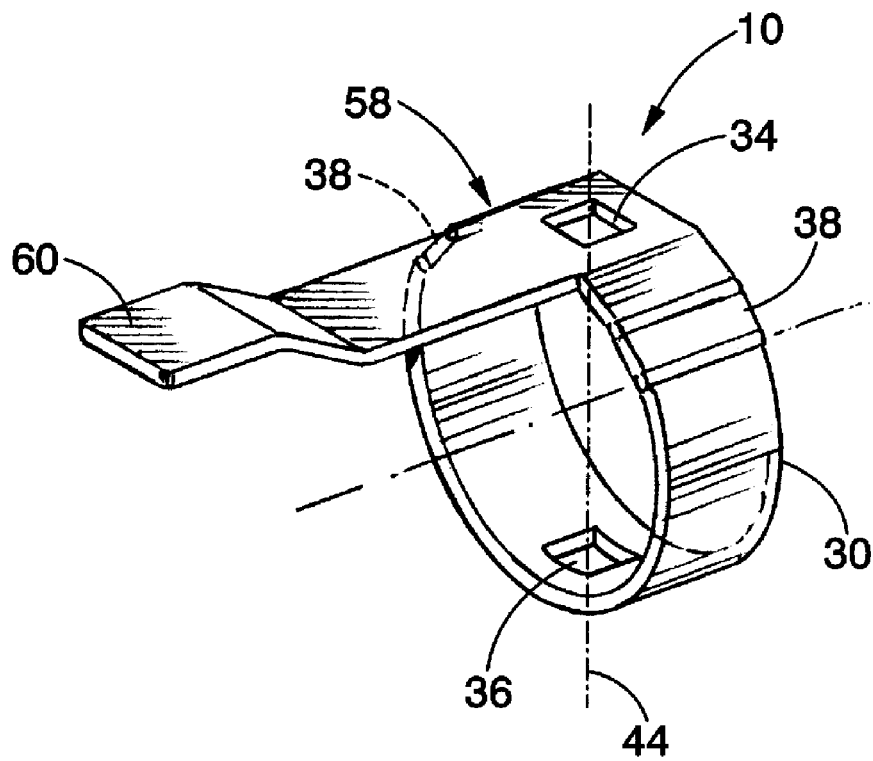

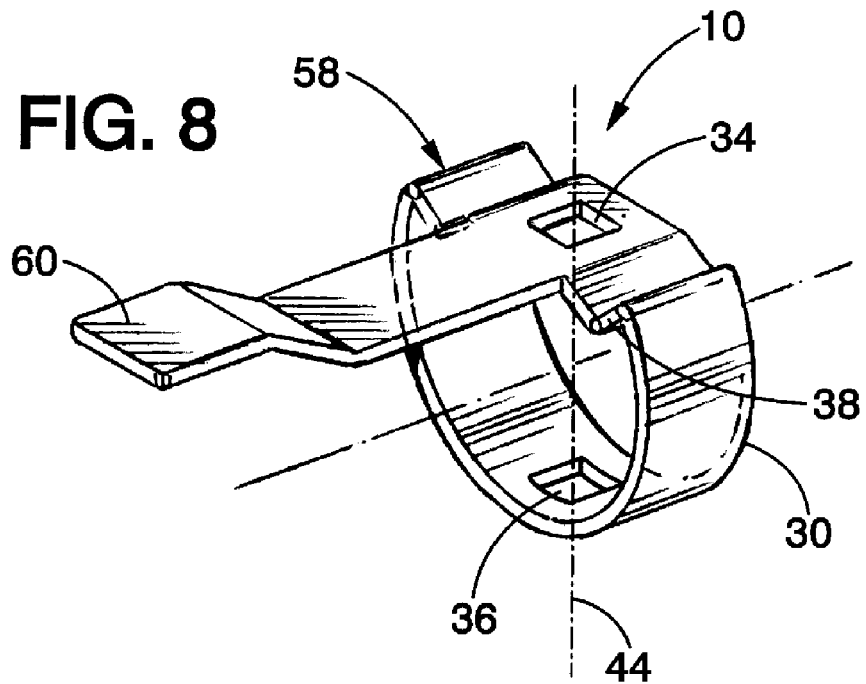
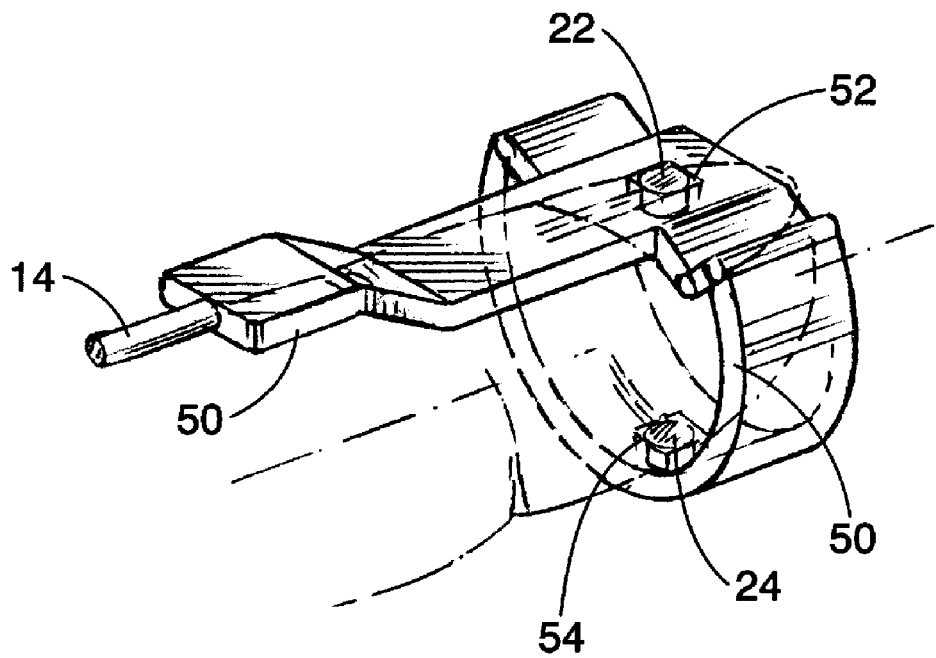

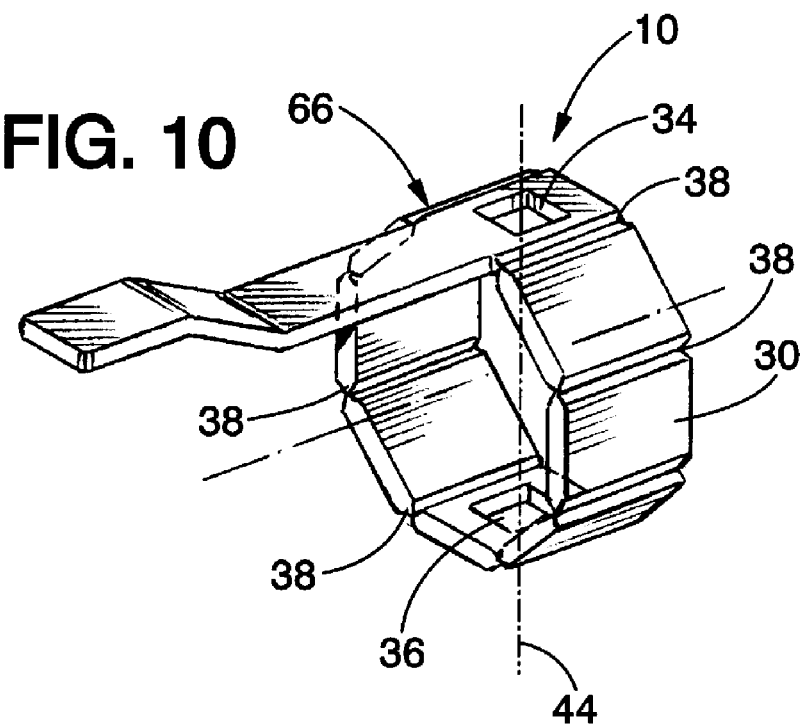
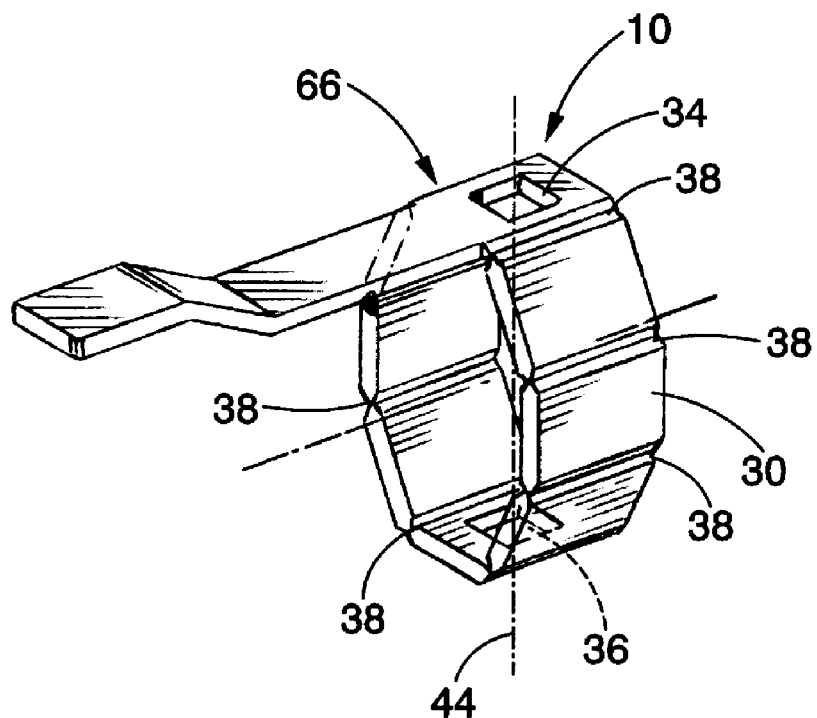

OPTICALLY ALIGNED PULSE OXIMETRY SENSOR AND TECHNIQUE FOR USING THE SAME

CROSS-REFERENCE TO RELATED APPLICATION

This application is a continuation of U.S. application Ser. No. 11/241,031, entitled "OPTICALLY ALIGNED PULSE OXIMETRY SENSOR AND TECHNIQUE FOR USING THE SAME," filed Sep. 30, 2005, which is herein incorporated by reference in its entirety for all purposes.

BACKGROUND OF THE INVENTION

1. Field of the Invention

The present invention relates generally to pulse oximetry and, more particularly, to sensors used for pulse oximetry.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

In many instances, it may be desirable to employ, for cost and/or convenience, a pulse oximeter sensor that is reusable. Such reusable sensors, however, should fit snugly enough that incidental patient motion will not dislodge or move the sensor yet not so tight that normal blood flow is disrupted, which may interfere with pulse oximetry measurements. Such a conforming fit may be difficult to achieve over a range of patient physiologies without adjustment or excessive attention on the part of medical personnel. In addition, for transmission-type pulse oximetry sensors (in which an emitter and detector are provided on opposite sides of the finger or toe) it may be difficult to maintain the desired alignment of optical components while obtaining a conforming fit. For example, it may be desirable to maintain the emitter and detector along a common axis, however, such alignment may be difficult to achieve or maintain while adjusting the sensor and its constituent components to fit a patient physiology.

SUMMARY

Certain aspects commensurate in scope with the originally claimed invention are set forth below. It should be understood that these aspects are presented merely to provide the reader with a brief summary of certain forms of the invention might take and that these aspects are not intended to limit the scope of the invention. Indeed, the invention may encompass a variety of aspects that may not be set forth below.

There is provided a sensor assembly that includes: a frame comprising one or more pair of flexible elements disposed substantially symmetric relative to an optical axis; at least two optical components disposed on the frame along the optical axis; and a covering provided over at least part of the frame and the at least two optical components.

There is provided a sensor assembly that includes: a frame; an emitter and a detector housed on the frame along an optical axis, wherein the emitter and the detector are configured to move relative to one another while remaining aligned along the optical axis; and a covering provided over the frame, the emitter, and the detector.

There is provided a method of manufacturing a sensor that includes: situating an emitter and a detector on a frame, wherein the frame comprises one or more pair of flexible elements disposed substantially symmetric relative to an optical axis upon which the emitter and the detector are situated; and coating the frame with a coating material to form a sensor assembly.

There is provided a method for acquiring physiological data that includes: emitting two or more wavelengths of light from an emitter of a sensor assembly disposed on a patient; detecting transmitted or reflected light using a photodetector of the sensor assembly, wherein the emitter and the photodetector are maintained in optical alignment with one another along an optical axis by one or more pair of flexible elements of the sensor assembly, wherein the one or more pair of flexible elements are disposed symmetrical to the optical axis; and determining a physiological parameter based on the detected light.

There is provided a method of manufacturing a sensor body that includes: coating a frame with a coating material to form a sensor body, wherein the frame comprises one or more pair of flexible elements disposed substantially symmetric relative to an optical axis defined by an emitter housing and a detector housing of the frame.

There is provided a sensor body, that includes: a frame comprising one or more pair of flexible elements disposed substantially symmetric relative to an optical axis defined by an emitter housing and a detector housing of the frame; and a covering provided over the frame.

There is provided a sensor body, that includes: a frame comprising an emitter housing and a detector housing which define an optical axis, wherein the emitter housing and the detector housing are configured to move relative to one another while remaining aligned along the optical axis; and a covering provided over the frame to form a sensor assembly.

There is provided a frame of a sensor, that includes: at least two optical component housings defining an optical axis; and one or more pair of flexible elements disposed substantially symmetric relative to the optical axis.

There is provided a frame of a sensor, that includes: an emitter housing and a detector housing which define an optical axis, wherein the emitter housing and the detector housing are configured to move relative to one another while remaining aligned along optical axis.

There is provided a method for manufacturing a frame of a sensor, that includes: forming at least two optical component housings of a frame of a sensor such that the at least two optical component housings define an optical axis; and providing one or more pair of flexible elements on the frame disposed substantially symmetric relative to the optical axis.

BRIEF DESCRIPTION OF THE DRAWINGS

Advantages of the invention may become apparent upon reading the following detailed description and upon reference to the drawings in which:

FIG. 2 illustrates a perspective view of one configuration of an internal frame for use in a patient sensor, in accordance with aspects of the present technique;

FIG. 3 illustrates the internal frame of FIG. 2 in an expanded configuration;

FIG. 4 illustrates the internal frame of FIG. 2 in a collapsed configuration;

FIG. 5 illustrates a perspective view of a covered patient sensor based upon the internal frame of FIG. 2;

FIG. 6 illustrates a perspective view of another configuration of an internal frame for use in a patient sensor, in accordance with aspects of the present technique;

FIG. 7 illustrates the internal frame of FIG. 6 in an expanded configuration;

FIG. 8 illustrates the internal frame of FIG. 6 in a collapsed configuration;

FIG. 9 illustrates a perspective view of a covered patient sensor based upon the internal frame of FIG. 6;

FIG. 10 illustrates a perspective view of a further configuration of an internal frame for use in a patient sensor, in accordance with aspects of the present technique;

FIG. 11 illustrates the internal frame of FIG. 10 in an expanded configuration;

DETAILED DESCRIPTION OF SPECIFIC EMBODIMENTS

Figure 1:
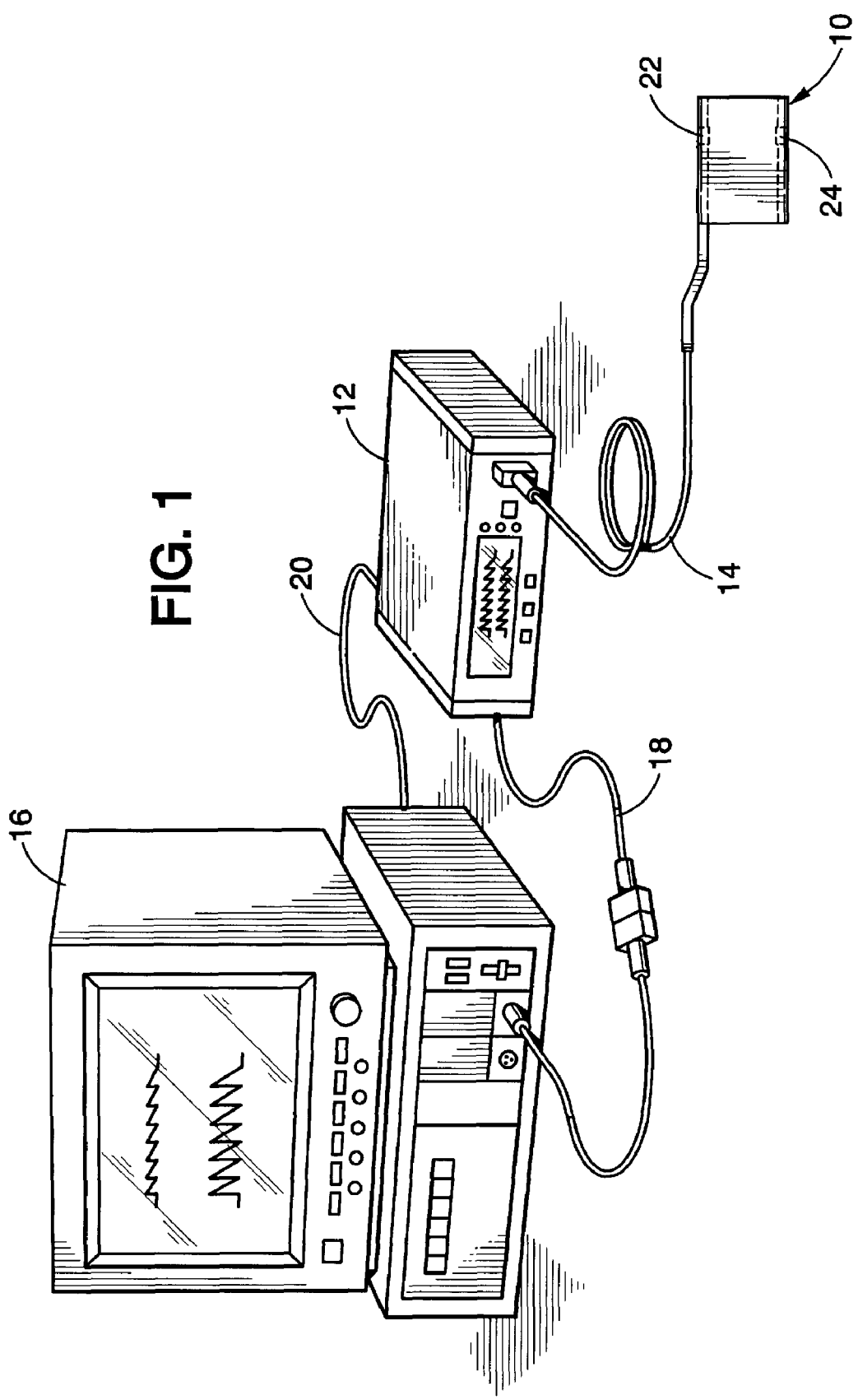
FIG. 1 illustrates a physiological monitoring system coupled to a multi-parameter patient monitor and a patient sensor, in accordance with aspects of the present technique.

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a comfortable and conformable reusable patient sensor that is easily cleaned and that maintains alignment between optical components. In accordance with some aspects of the present technique, a reusable patient sensor is provided that includes a flexible frame, such as a framework incorporating living hinges, pin hinges, bar links, bending beams, and so forth, which allows the patient sensor to conform to fingers or toes of varying sizes while maintaining alignment of the optical components.

Prior to discussing such exemplary sensors in detail, it should be appreciated that such sensors are typically designed for use with a patient monitoring system. For example, referring now to FIG. 1, a sensor 10 according to the present invention may be used in conjunction with a patient monitor 12. In the depicted embodiment, a cable 14 connects the sensor 10 to the patient monitor 12. As will be appreciated by those of ordinary skill in the art, the sensor 10 and/or the cable 14 may include or incorporate one or more integrated circuit devices or electrical devices, such as a memory, processor chip, or resistor that may facilitate or enhance communication between the sensor 10 and the patient monitor 12. Likewise the cable 14 may be an adaptor cable, with or without an integrated circuit or electrical device, for facilitating communication between the sensor 10 and various types of monitors, including older or newer versions of the patient monitor 12 or other physiological monitors. In other embodiments, the sensor 10 and the patient monitor 12 may communicate via wireless means, such as using radio, infrared, or optical signals. In such embodiments, a transmission device (not shown) may be connected to the sensor 10 to facilitate wireless transmission between the sensor 10 and the patient monitor 12. As will be appreciated by those of ordinary skill in the art, the cable 14 (or corresponding wireless transmissions) are typically used to transmit control or timing signals from the monitor 12 to the sensor 10 and/or to transmit acquired data from the sensor 10 to the monitor 12. In some embodiments, however, the cable 14 may be an optical fiber that allows optical signals to be conducted between the monitor 12 and the sensor 10.

In one embodiment, the patient monitor 12 may be a suitable pulse oximeter, such as those available from Nellcor Puritan Bennett Inc. In other embodiments, the patient monitor 12 may be a monitor suitable for measuring tissue water fractions, or other body fluid related metrics, using spectrophotometric or other techniques. Furthermore, the monitor 12 may be a multi-purpose monitor suitable for performing pulse oximetry and measurement of tissue water fraction, or other combinations of physiological and/or biochemical monitoring processes, using data acquired via the sensor 10. Furthermore, to upgrade conventional monitoring functions provided by the monitor 12 to provide additional functions, the patient monitor 12 may be coupled to a multi-parameter patient monitor 16 via a cable 18 connected to a sensor input port and/or via a cable 20 connected to a digital communication port.

The sensor 10, in the example depicted in FIG. 1, may be covered to provide a unitary or enclosed assembly. Such covering, however, is optional. The sensor 10, includes an emitter 22 and a detector 24 which may be of any suitable type. For example, the emitter 22 may be one or more light emitting diodes adapted to transmit one or more wavelengths of light, such as in the red to infrared range, and the detector 24 may be a photodetector, such as a silicon photodiode package, selected to receive light in the range emitted from the emitter 22. In the depicted embodiment, the sensor 10 is coupled to a cable 14 that is responsible for transmitting electrical and/or optical signals to and from the emitter 22 and detector 24 of the sensor 10. The cable 14 may be permanently coupled to the sensor 10, or it may be removably coupled to the sensor 10—the latter alternative being more useful and cost efficient in situations where the sensor 10 is disposable.

The sensor 10 described above is generally configured for use as a "transmission type" sensor for use in spectrophotometric applications. As will be appreciated by those of ordinary skill in the art, however, such discussion is merely exemplary and is not intended to limit the scope of the present technique. Transmission type sensors include an emitter and detector that are typically placed on opposing sides of the sensor site. If the sensor site is a fingertip, for example, the sensor 10 is positioned over the patient's fingertip such that the emitter and detector lie on either side of the patient's nail bed. For example, the sensor 10 is positioned so that the emitter is located on the patient's fingernail and the detector is located opposite the emitter on the patient's finger pad. During operation, the emitter shines one or more wavelengths of light through the patient's fingertip, or other tissue, and the light received by the detector is processed to determine various physiological characteristics of the patient.

For pulse oximetry applications using transmission type sensors the oxygen saturation of the patient's arterial blood may be determined using two or more wavelengths of light, most commonly red and near infrared wavelengths. Similarly, in other applications a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of infrared, visible, ultraviolet, or even X-ray electromagnetic radiation, and may also include any wavelength within the infrared, visible, ultraviolet, or X-ray spectra.

Pulse oximetry and other spectrophotometric sensors are typically placed on a patient in a location conducive to measurement of the desired physiological parameters. For example, pulse oximetry sensors are typically placed on a patient in a location that is normally perfused with arterial blood to facilitate measurement of the desired blood characteristics, such as arterial oxygen saturation measurement ($SaO_2$). Common pulse oximetry sensor sites include a patient's fingertips, toes, forehead, or earlobes. Regardless of the placement of the sensor 10, the reliability of the pulse oximetry measurement is related to the accurate detection of transmitted light that has passed through the perfused tissue and has not been inappropriately supplemented by outside light sources or modulated by subdermal anatomic structures. Such inappropriate supplementation and/or modulation of the light transmitted by the sensor can cause variability in the resulting pulse oximetry measurements.

Referring now to FIGS. 2-13, the sensor 10 is discussed in greater detail. For example, in FIGS. 2-4, a first configuration 28 of an exemplary frame 30 for a sensor 10 is depicted. Such a frame 30 may provide an internal structure that defines the general shape of the sensor 10 when covered, such as by overmolding, to form the patient sensor 10. In such an embodiment, the frame 30 may provide a general structure and range of motion for the patient sensor 10 while the covering may provide a surface area which contacts the patient and may protect the frame 30 and optical components of the patient sensor 10. In view of the various structural and motion functions performed by the frame 30, different structures or regions of the frame 30 may have similar or different rigidities or other mechanical properties.

The frame 30 may include various structural features such as a cable guide through which a cable, such as an electrical or optical cable, may pass to connect to the electrical or optical conductors attached to the emitter 22 and/or detector 24 upon assembly. Likewise, the frame 30 may include component housings, such as the emitter housing 34 and detector housing 36. In addition, the frame 30 may include flexible components or elements 38, such as living hinges, pin hinges, bar links, bending beams, and so forth, which facilitate the motion of the emitter housing 34 and/or the detector housing 36 relative to one another.

In certain embodiments, the frame 30 is constructed, in whole or in part, from polymeric materials, such as thermoplastics, capable of providing a suitable rigidity or semi-rigidity for the different portions of the frame 30. Examples of such suitable materials include polyurethane, polypropylene, and nylon, though other polymeric materials may also be suitable. In other embodiments, the frame 30 is constructed, in whole or in part, from other suitably rigid or semi-rigid materials that provide the desired support and flexibility, such as stainless steel, aluminum, magnesium, graphite, fiberglass, or other metals, alloys, or compositions that are sufficiently ductile and/or strong. For example, metals, alloys, or compositions that are suitable for diecasting, sintering, lost wax casting, stamping and forming, and other metal or composition fabrication processes may be used to construct the frame 30.

In addition, the frame 30 may be constructed as an integral structure or as a composite structure. For example, in one embodiment, the frame 30 may be constructed as a single piece from a single material or from different materials. Alternatively, the frame 30 may be constructed or assembled as a composite structure from two or more parts that are separately formed. In such embodiments, the different parts may be formed from the same or different materials. For example, in implementations where different parts are formed from different materials, each part may be constructed from a material having suitable mechanical and/or chemical properties for that part. The different parts may then be joined or fitted together to form the frame 30, such as by a snap fitting process, ultrasonic welding, heat staking or by application of an adhesive or mechanical fastener.

For example, the flexible elements 38, such as living hinges, pin hinges, bar links, bending beams, and so forth, may be constructed from the same materials and/or from different materials than the remainder of the frame 30. Furthermore, the flexible elements 38 may be formed integrally with the remainder of the frame 30. For example, in one embodiment, the frame 30 may be molded from polymeric materials as one piece, with the flexible elements 38 formed as living hinges molded from the polymeric material. Alternatively, some or all of the flexible elements 38 may be molded or formed as separate pieces that are attached to the remainder of the frame structure. In such embodiments, the flexible elements 38 may be formed from the same or different materials and the remainder of the frame 30 and may serve to hold different portions of the frame structure together. For example, in an embodiment in which the flexible elements 38 are pin hinges, the frame sides 42 may be formed from polymeric materials and may include annular structures along their edges that are complementary to the annular structures of an adjacent frame side 42. In such an embodiment, a pin, such as a metal pin, may be fitted through the annular structures of two adjacent frame sides 42, thereby forming an attachment and a hinge upon which the attached frame sides 42 may be moved. As will be appreciated by those of ordinary skill in the art, other suitable hinge and/or attachment techniques may also be applicable to construct the frame 30.

Furthermore, the frame 30 may be molded, formed, or constructed in a different configuration than the final sensor configuration. For example, the frame 30 for use in the sensor 10 may be initially formed, from one or more pieces, in a generally open, or flat, configuration compared to the relatively closed configuration of the frame 30 when folded to form the sensor 10. In such embodiments, the frame 30 may be formed generally open or planar and then folded or bent, such as at the flexible regions 38, into the closed configuration associated with the sensor 10. A covering may be applied, such as by overmolding, prior to or subsequent to folding or bending the frame 30 from the open configuration to the closed configuration. In such an embodiment, the frame 30 may be secured together as described above, such as via a snap fitting process or via other techniques suitable for attaching the respective portions of the frame 30 including ultrasonic welding, heat staking or by application of an adhesive or mechanical fastener.

In the example depicted in FIGS. 2-4, a first configuration 28 of the frame 30 is provided. In the first configuration 28, the flexible regions 38 are provided in pairs that are symmetric about a vertical place that coincides with the optical axis 44. The paired, symmetric flexible regions 38 allow lineal expansion and/or contraction along the optical axis 44, thereby maintaining optical alignment of the emitter 22 and detector 24 as the frame 30 expands or collapses to conformably fit a patient's digit. In addition, the flexible regions 38 may allow lateral expansion (i.e., transverse to the optical axis) of the frame 30 to provide a laterally conforming fit to differently sized fingers and toes.

For example, referring now to FIG. 3, the first configuration 28 of FIG. 2 is depicted as expanded along the optical axis 44 between the emitter 22 and detector 24, such as to accommodate a large finger or toe needing greater vertical space. The paired, symmetric flexible regions 38 constrain the range of motion of the emitter 22 and detector 24 to linear motion along the optical axis 44, thereby maintaining the emitter 22 and detector 24 in alignment despite there motion relative to one another. Similarly, referring now to FIG. 4, the first configuration 28 is depicted as collapsed along the optical axis 44, such as to accommodate a smaller finger or toe, while maintaining alignment of the emitter 22 and detector 24 along the optical axis 44.

As noted above, in certain embodiments of the present technique, the frame 30 (such as the first configuration 28 of the frame 30) may be covered to form a unitary or integral sensor assembly or sensor body, as depicted in FIG. 5. Such covered embodiments may result in a sensor assembly in which the internal frame 30 is completely or substantially covered by a covering material 50. In embodiments in which the internal frame 30 is formed or molded as a relatively open or flat structure, the covering process may be performed prior to or subsequent to bending the internal frame 30 into the closed configuration.

For example, the sensor 10 may be formed by an injection molding process. In one example of such a process the internal frame 30 may be positioned within a die or mold of the desired shape for the sensor 10. A molten or otherwise unset overmold material may then be injected into the die or mold. For example, in one implementation, a molten thermoplastic elastomer at between about 400° F. to about 450° F. is injected into the mold. The coating material may then be set, such as by cooling for one or more minutes or by chemical treatment, to form the sensor body about the internal frame 30. In certain embodiments, other sensor components, such as the emitter 22 and/or detector 24, may be attached or inserted into their respective housings or positions on the overmolded sensor body.

Alternatively, the optical components (such as emitter 22 and detector 24) and/or conductive structures (such as wires or flex circuits) may be placed on the internal frame 30 prior to overmolding. The internal frame 30 and associated components may then be positioned within a die or mold and overmolded, as previously described. To protect the emitter 22, detector 24, and or other electrical components, conventional techniques for protecting such components from excessive temperatures may be employed. For example, the emitter 22 and/or the detector 24 may include an associated clear window, such as a plastic or crystal window, in contact with the mold to prevent coating 50 from being applied over the window. In one embodiment, the material in contact with such windows may be composed of a material, such as beryllium copper, which prevents the heat of the injection molding process from being conveyed through the window to the optical components. For example, in one embodiment, a beryllium copper material initially at about 40° F. is contacted with the windows associated with the emitter 22 and/or detector 24 to prevent coating of the windows and heat transfer to the respective optical components.

As will be appreciated by those of ordinary skill in the art, the injection molding process described herein is merely one technique by which the frame 30 may be covered to form a sensor body, with or without associated sensing components. Other techniques which may be employed include, but are not limited to, dipping the frame 30 into a molten or otherwise unset coating material to coat the frame 30 or spraying the frame 30 with a molten or otherwise unset coating material to coat the frame 30. In such implementations, the coating material may be subsequently set, such as by cooling or chemical means, to form the coating. Such alternative techniques, to the extent that they may involve high temperatures, may include thermally protecting whatever optical components are present, such as by using beryllium copper or other suitable materials to prevent heat transfer through the windows associated with the optical components, as discussed above.

The frame 30 may be covered by other techniques as well. For example, the covering material 50 may be a sheet, a sleeve, or a film material which is applied to the frame. Such a covering material 50 may be bonded, such as with an adhesive material, or mechanically fastened to the frame 30. For instance, a suitable film material may be an extruded or laminated film that is adhesively or mechanically bonded to the frame 30. Likewise, a suitable sheet material may be a single or multi-layer sheet material that is adhesively or mechanically bonded to the frame 30. Other exemplary covering material 50 include cast, foamed, or extruded materials suitable for attachment to the frame 30.

By such techniques, the frame 30, as well as the optical components and associated circuitry where desired, may be encased in a covering material 50 to form an integral or unitary assembly with no exposed or external moving parts of the internal frame 30. For example, as depicted in FIG. 5, the sensor 10 includes features of the underlying internal frame 30 that are now completely or partially covered, such as the overmolded emitter housing 52 and detector housing 54.

In one implementation, the covering material 50 is a thermoplastic elastomer or other conformable coating or material. In such embodiments, the thermoplastic elastomer may include compositions such as thermoplastic polyolefins, thermoplastic vulcanizate alloys, silicone, thermoplastic polyurethane, and so forth. As will be appreciated by those of ordinary skill in the art, the overmolding composition may vary, depending on the varying degrees of conformability, durability, wettability, or other physical and/or chemical traits that are desired.

Furthermore, the covering material 50 may be selected based upon the desirability of a chemical bond between the internal frame 30 and the covering material 50. Such a chemical bond may be desirable for durability of the resulting sensor 10. For example, to prevent separation of the covering material 50 from the internal frame 30, a covering material 50 may be selected such that the covering material 50 bonds with some or all of the internal frame 30. In such embodiments, the covering material 50 and the portions of the internal frame 30 to which the covering material 50 is bonded are not separable, i.e., they form one continuous and generally inseparable structure.

Furthermore, in embodiments in which the covering material 50 employed is liquid or fluid tight, such a sensor 10 may be easily maintained, cleaned, and/or disinfected by immersing the sensor into a disinfectant or cleaning solution or by rinsing the sensor 10 off, such as under running water. In particular, such an covered sensor assembly may be generally or substantially free of crevices, gaps, junctions or other surface irregularities typically associated with a multi-part construction which may normally allow the accumulation of biological detritus or residue. Such an absence of crevices and other irregularities may further facilitate the cleaning and care of the sensor 10.

In the depicted example, flexible regions 38 of the frame 30 incorporated into the sensor 10 (in either coated or uncoated embodiments) provide vertical and/or lateral accommodation of a finger or other patient digit, and thereby providing a conforming fit. Furthermore, in the depicted embodiment, the lateral sides of the frame 30 (or the covering material 50 disposed over such lateral sides) facilitate the exclusion of environmental or ambient light from the interior of the sensor 10. The lateral sides of the sensor 10, therefore, help prevent or reduce the detection of light from the outside environment, which may be inappropriately detected by the sensor 10 as correlating to the $SaO_2$. Thus, the pulse oximetry sensor may detect differences in signal modulations unrelated to the underlying $SaO_2$ level. In turn, this may impact the detected red-to-infrared modulation ratio and, consequently, the measured blood oxygen saturation ($SpO_2$) value. The conformability of the fit of sensor 10 and the presence of the lateral sides on the sensor 10, therefore, may help prevent or reduce such errors.

While the frame 30 in the first configuration 28 may be used to form a covered or uncovered sensor 10, other frame configurations may also be used in accordance with the present technique. For example, referring now to FIGS. 6-8, a second frame configuration 58 is depicted. The exemplary second frame configuration 58 includes components noted above with regard to the first configuration 28, such as a symmetric pair of flexible regions 38, an emitter housing 34, and a detector housing 36, as well as a cable guide 60.

In the embodiment depicted in FIGS. 6-8, the second configuration 58 of the frame 30 is provided as a semi-rigid, generally annular structure upon which the emitter housing 34 and detector housing 36 are disposed opposite one another. Between the emitter housing 34 and detector housing 36, a symmetric pair of flexible regions 38 (as discussed with regard to FIGS. 2-4) is disposed. The flexible regions 38 function as discussed above, allowing the emitter housing 34 (and associated emitter 22) and detector housing 36 (and associated detector 24) to move relative to one another along the optical axis 44. In this manner, alignment of optical components, such as an emitter 22 and detector 24 may be maintained while obtaining a conforming fit to a patient's digit. While the second configuration of FIG. 6 is depicted with one pair of symmetrical flexible regions 38, one of ordinary skill in the art will appreciate that additional flexible regions 38 may be provided on the second configuration 58 of the frame 30 to maintain optical alignment of the emitter 22 and detector 24.

Referring now to FIG. 7, the second configuration 58 of the frame 30 is depicted as expanded along the optical axis 44 between the emitter 22 and detector 24, such as to accommodate a large finger or toe needing greater vertical space. The paired, symmetric flexible regions 38 constrain the range of motion of the emitter 22 and detector 24 to linear motion along the optical axis 44, thereby maintaining the emitter 22 and detector 24 in alignment despite there motion relative to one another. Similarly, in FIG. 8, the second configuration 58 is depicted as collapsed along the optical axis 44, such as to accommodate a smaller finger or toe, while maintaining alignment of the emitter 22 and detector 24 along the optical axis 44.

The second configuration 58 of the frame 30 is depicted as covered in FIG. 9. The techniques and materials that may be used to cover the second configuration 58 of the frame 30 are the same or similar to those discussed above with regard to the covered first configuration 28 of frame 30 discussed in relation to FIG. 5. Likewise the covered structures and benefits are the same or similar to those discussed above with regard to the covered configuration of FIG. 5. In this manner, a unitary sensor or sensor body may be constructed about the second configuration 58 of the frame 30 that provides a conforming fit while maintaining the optical alignment of the optical components.

Other frame configurations incorporating aspects of the present technique are also possible. For example, referring now to FIGS. 10-12, a third frame configuration 66 is depicted. The exemplary third frame configuration 66 includes components noted above with regard to the first and second configurations 28 and 58, such as symmetric pairs of flexible regions 38, an emitter housing 34, and a detector housing 36.

Figure 12:
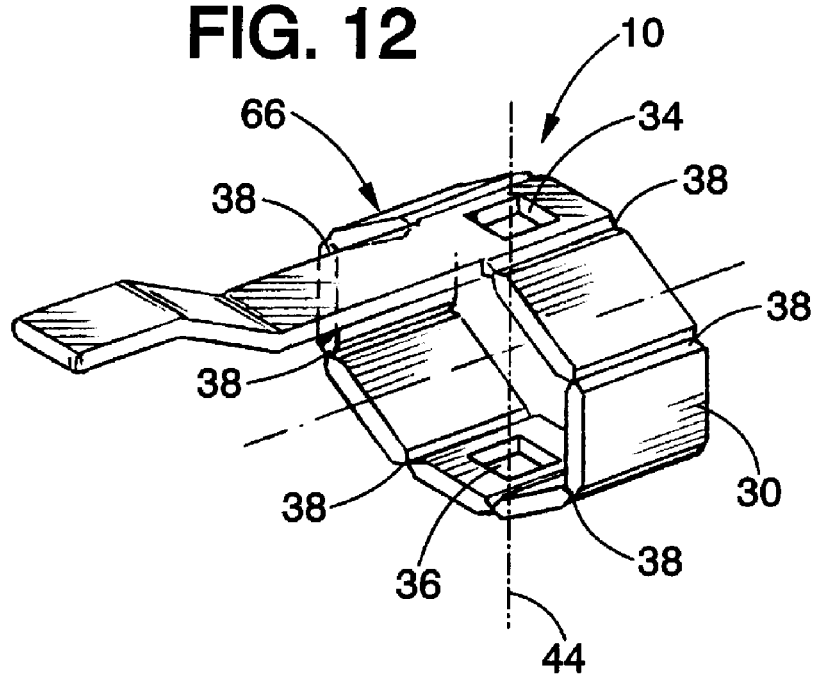
FIG. 12 illustrates the internal frame of FIG. 10 in a collapsed configuration.

In the embodiment depicted in FIGS. 10-12, the third configuration 66 of the frame 30 is provided as a hinged, loop structure upon which the emitter housing 34 and detector housing 36 are disposed opposite one another. Between the emitter housing 34 and detector housing 36, four symmetric pairs of flexible regions 38 is disposed. The flexible regions 38 function as discussed above, allowing the emitter housing 34 (and associated emitter 22) and detector housing 36 (and associated detector 24) to move relative to one another along the optical axis 44. In this manner, alignment of optical components, such as an emitter 22 and detector 24 may be maintained while obtaining a conforming fit to a patient's digit. While the third configuration of FIG. 10 is depicted with four pairs of symmetrical flexible regions 38, one of ordinary skill in the art will appreciate that less than or more than four flexible regions 38 may be provided on the third configuration 66 of the frame 30 to maintain optical alignment of the emitter 22 and detector 24.

Referring now to FIG. 11, the third configuration 66 of the frame 30 is depicted as expanded along the optical axis 44 between the emitter 22 and detector 24, such as to accommodate a large finger or toe needing greater vertical space. The paired, symmetric flexible regions 38 constrain the range of motion of the emitter 22 and detector 24 to linear motion along the optical axis 44, thereby maintaining the emitter 22 and detector 24 in alignment despite there motion relative to one another. Similarly, in FIG. 12, the third configuration 66 is depicted as collapsed along the optical axis 44, such as to accommodate a smaller finger or toe, while maintaining alignment of the emitter 22 and detector 24 along the optical axis 44.

Figure 13:
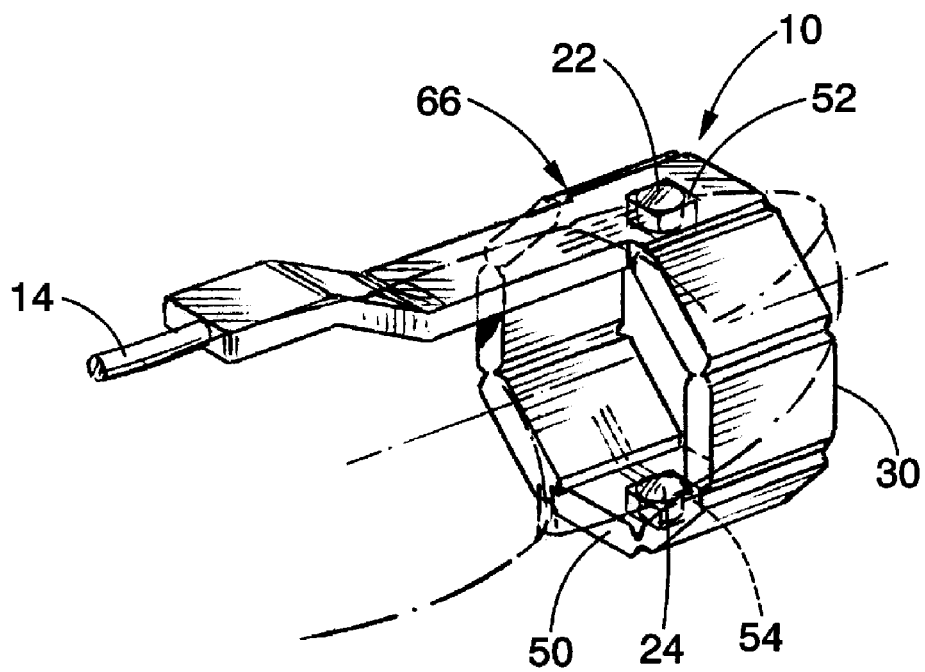
FIG. 13 illustrates a perspective view of a covered patient sensor based upon the internal frame of FIG. 10.

The third configuration 66 of the frame 30 is depicted as covered in FIG. 13. The techniques and materials that may be used to cover the third configuration 66 of the frame 30 are similar to those discussed above with regard to the covered first configuration 28 of frame 30 discussed in relation to FIG. 5. Likewise the covered structures and benefits are the same or similar to those discussed above with regard to the covered configuration of FIG. 5. In this manner, a unitary sensor or sensor body may be constructed about the third configuration 66 of the frame 30 that provides a conforming fit while maintaining the optical alignment of the optical components.

While the exemplary medical sensors 10 discussed herein are provided as examples, other such devices are also contemplated and fall within the scope of the present disclosure. For example, other medical sensors and/or contacts applied externally to a patient may be advantageously applied using an covered sensor body as discussed herein. Examples of such sensors or contacts may include glucose monitors or other sensors or contacts that are generally held adjacent to the skin of a patient such that a conformable and comfortable fit is desired. Similarly, and as noted above, devices for measuring tissue water fraction or other body fluid related metrics may utilize a sensor as described herein. Likewise, other spectrophotometric applications where a probe is attached to a patient may utilize a sensor as described herein.

Furthermore, though the preceding discussion notes the possibility of covering the frame 30 with an overmold material to construct the sensor 10 or the sensor body, one of ordinary skill in the art will appreciate that the frame 30 may also be used without such a covering. For example, the frame 30 may itself form a sensor body, with optical components such as the emitter 22 and/or detector 24 being added to the frame 30 to form the sensor 10. In such an embodiment, an adhesive strip or bandage may help secure the sensor 10 to the patient.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present techniques may not only be applied to transmission type sensors for use in pulse oximetry, but also to retroflective and other sensor designs as well. Likewise, the present techniques are not limited to use on fingers and toes but may also be applied to placement on other body parts such as in embodiments configured for use on the ears or nose.

What is claimed is:

1. A sensor assembly, comprising:
a frame comprising at least two rigid or semirigid portions coupled to one or more pairs of flexible hinge elements, wherein the one or more pairs of flexible hinge elements are disposed substantially symmetric relative to an optical axis and are configured to allow the frame to expand and contract along the optical axis; and
at least two housings configured to hold optical components disposed on the at least two rigid or semirigid portions of the frame, respectively, along the optical axis, wherein the at least two housings are configured to move along the optical axis without changing orientation relative to one another as the frame expands and contracts along the optical axis.

2. The sensor assembly of claim 1, wherein the one or more pairs of flexible hinge elements comprise one or more pairs of living hinges, pin hinges, or bar links.

3. The sensor assembly of claim 1, wherein the frame comprises one or more of a thermoplastic material, a metal, a metallic alloy, or a composite material.

4. The sensor assembly of claim 1, wherein the at least two housings comprise an emitter housing configured to receive an emitter and a detector housing configured to receive a detector.

5. The sensor assembly of claim 1, wherein the at least two rigid or semirigid portions comprise an annular structure.

6. The sensor assembly of claim 1, wherein the at least two rigid or semirigid portions comprise a plurality of flat sides.

7. The sensor assembly of claim 6, wherein the one or more pairs of flexible hinge elements are configured to constrain opposing flat sides of the plurality of flat sides of the frame to remain substantially parallel to one another as the frame expands and contracts along the optical axis.

8. A sensor assembly, comprising:
a frame comprising two or more pairs of rigid or semirigid flat pieces and a plurality flexible hinge elements, wherein each pair of flat pieces comprises a first flat piece disposed on an opposite side of the frame from a second flat piece, and wherein the flexible hinge elements enable the first and the second flat pieces of each of the two or more pairs of flat pieces to remain substantially parallel to one another as the frame expands and contracts; and
an emitter housing and a detector housing respectively disposed on the first and second flat pieces of one of the two or more pairs of flat pieces, wherein the flexible hinge elements enable the one of the two or more pairs of flat pieces to move toward and away from one another as the frame expands and contracts.

9. The sensor assembly of claim 8, wherein the frame comprises one or more of a thermoplastic material, a metal, a metallic alloy, or a composite material.

10. The sensor assembly of claim 8, wherein the plurality of flexible hinge elements are disposed substantially symmetric relative to an optical axis defined by the emitter housing and the detector housing.

11. The sensor assembly of claim 8, comprising at least one integrated circuit device.

12. The sensor assembly of claim 8, comprising an emitter disposed in the emitter housing configured to emit two or more wavelengths of light; and comprising a detector disposed in the detector housing and configured to detect the light emitted from the emitter.

13. A system, comprising:
a monitor; and
a sensor configured to transmit signals to and from the monitor, the sensor comprising:
a frame comprising at least two rigid or semirigid portions coupled to one or more pairs of flexible hinge elements, wherein the one or more pairs flexible hinge elements are disposed substantially symmetric relative to an optical axis and are configured to allow the frame to expand and contract along the optical axis; and
at least two housings configured to hold optical components respectively disposed on the at least two rigid or semirigid portions of the frame along the optical axis, wherein the at least two housings are configured to move along the optical axis without altering an orientation of the at least two housings relative to one another as the frame expands and contracts along the optical axis.

14. The system of claim 13, wherein the at least two housings comprise an emitter housing and a detector housing.

15. The system of claim 14, wherein the sensor comprises an emitter disposed in the emitter housing and a detector disposed in the detector housing, and wherein the emitter is configured to emit at least two wavelengths of light, and wherein the detector is configured to detect the light emitted from the emitter.

16. The system of claim 12, wherein the one or more pairs of flexible hinge elements comprise one or more pair of living hinges, pin hinges, or bar links.

17. The system of claim 13, wherein the monitor comprises a pulse oximetry monitor.

18. A sensor, comprising:
a frame comprising a first rigid or semirigid annular portion coupled to a second rigid or semirigid portion by at least one pair of flexible hinge elements, wherein the at least one pair of flexible hinge elements is disposed substantially symmetric relative to an optical axis and is configured to allow the frame to expand and contract along the optical axis; and
an emitter housing and a detector housing disposed on the first or second rigid or semirigid portions of the frame along the optical axis, wherein the emitter housing and the detector housing are configured to move relative to one another while remaining aligned along the optical axis.

19. The sensor of claim 18, wherein the sensor comprises a covering provided over the frame, the emitter housing, and the detector housing.

20. The sensor of claim 18, comprising an emitter disposed in the emitter housing configured to emit two or more wavelengths of light; and comprising a detector disposed in the detector housing and configured to detect the light emitted from the emitter.

* * * * *